United States Patent [19]

Naylor

[11] 4,117,848
[45] Oct. 3, 1978

[54] CARDIAC INSTRUMENTATION APPARATUS WITH PACER DIAGNOSTICS

[75] Inventor: Thomas Kipling Naylor, Belmont, Mass.

[73] Assignee: American Optical Corporation, Southbridge, Mass.

[21] Appl. No.: 820,523

[22] Filed: Aug. 1, 1977

[51] Int. Cl.² ............................................. A61N 1/36
[52] U.S. Cl. ............................ 128/419 PT; 128/2.06 R
[58] Field of Search ........ 128/419 PT, 419 A, 2.06 B, 128/2.06 R

[56] References Cited

U.S. PATENT DOCUMENTS

| 3,651,799 | 3/1972 | Daynard | 128/419 PT |
| 3,871,363 | 3/1975 | Day | 128/419 PT |
| 3,872,252 | 3/1975 | Malchman et al. | 128/419 PT |
| 3,923,041 | 12/1973 | Stasz et al. | 128/419 PT |
| 4,055,189 | 10/1977 | Puerbach et al. | 128/419 PT |

Primary Examiner—William E. Kamm
Attorney, Agent, or Firm—Jeremiah J. Duggan; Stephen A. Schneeberger

[57] ABSTRACT

In an EKG monitor capable of monitoring the stimulation pulse of a heart pacer, the inclusion of means for determining the polarity of the pacer pulse detected in the ECG signal and then for generating a standardized pacer pulse signal of the same polarity as detected. The apparatus further includes summing means for summing the ECG signal with the standardized pacer pulse to be included in the output of the monitor.

8 Claims, 14 Drawing Figures

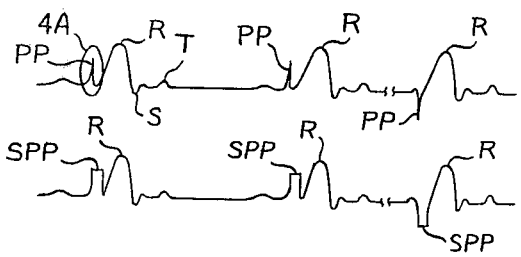
Fig. 3A
Fig. 3B
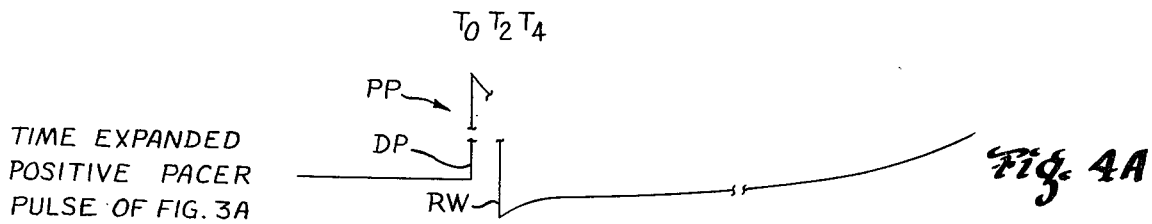
TIME EXPANDED
POSITIVE PACER
PULSE OF FIG. 3A
Fig. 4A
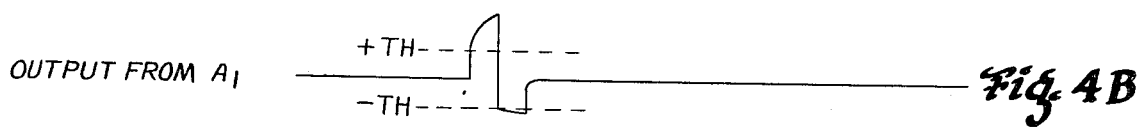
OUTPUT FROM $A_1$
Fig. 4B
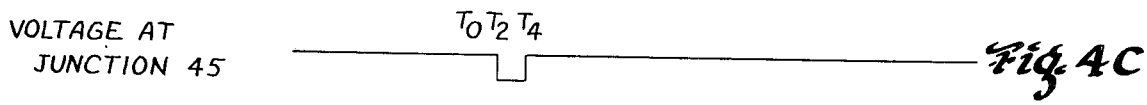
VOLTAGE AT
JUNCTION 45
Fig. 4C
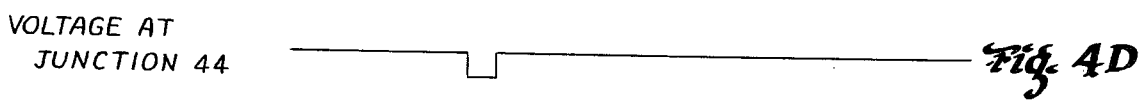
VOLTAGE AT
JUNCTION 44
Fig. 4D
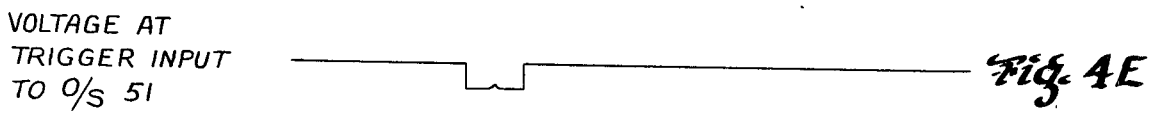
VOLTAGE AT
TRIGGER INPUT
TO O/S 51
Fig. 4E
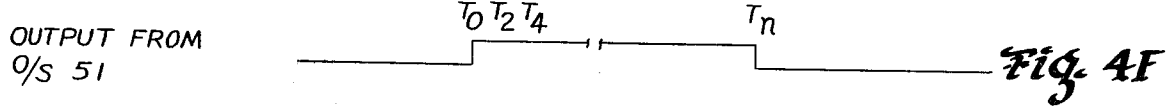
OUTPUT FROM
O/S 51
Fig. 4F
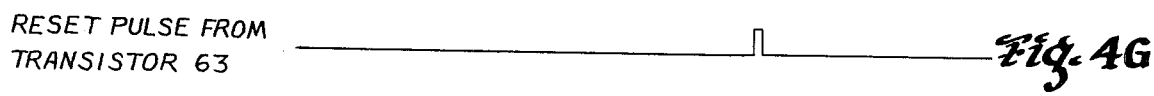
RESET PULSE FROM
TRANSISTOR 63
Fig. 4G
Q OUTPUT OF
D-FLOP 53
Fig. 4H
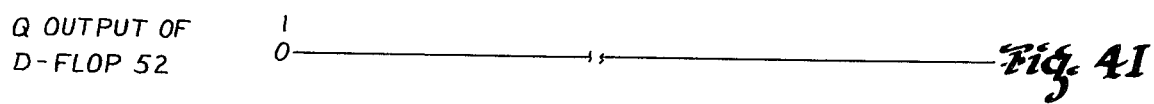
Q OUTPUT OF
D-FLOP 52
Fig. 4I
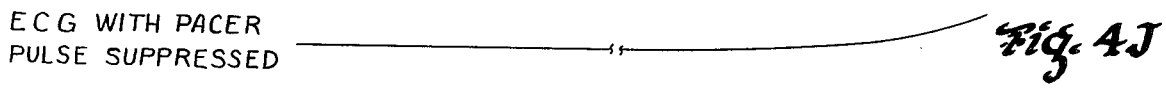
ECG WITH PACER
PULSE SUPPRESSED
Fig. 4J

CARDIAC INSTRUMENTATION APPARATUS WITH PACER DIAGNOSTICS

BACKGROUND OF THE INVENTION

This invention relates to cardiac instrumentation apparatus, and more particularly to such apparatus having a pacer diagnostic capability, as for use with visual displays and the like.

The use of cardiac pacers to assist the heart in certain types of heart disease is well known. Such cardiac pacers provide an electrical stimulation pulse to the heart, hereinafter referred to generally as "pacer pulse". The pacer pulse will include a discharge pulse responsible for stimulation and may also include a recharge waveform or tail immediately following the discharge pulse. When the heart beats normally or in response to an electrical stimulation pulse, it provides an electrical waveform called an electrocardiogram pulse, hereinafter referred to as "ECG signals."

In the ECG signal of a patient equipped with a pacer, the pacer pulse usually appears prior to QRS waveforms in the overall signal. The pacer pulse may be of large or small amplitude but of very small width, typically having a duration of 1 or 2 milliseconds. It is often desirable for various monitoring and/or analytical purposes, to clearly indicate the existence and/or width of the pulse, however, because of its very small width and sometimes small amplitude, it has been difficult to repeatedly and accurately detect the present of a pacer pulse in the ECG display.

The prior art has provided several techniques for augmenting the pacer pulse as it appears in a final dislay and/or for telephonic transmission. One example is illustrated in U.S. Pat. No. 3,871,363, issued Mar. 18, 1975 for Pacer Diagnostic Instrument by Christopher C. Day. That patent describes apparatus for generating an artificial pacer pulse in response to detection of an original pacer pulse, which artificial pacer pulse is of substantially greater duration than the original pacer pulse and having a duration which may vary in proportion to the duration of the original pacer pulse. This is particularly desirable when providing for permanent recording of the ECG signal on a paper recorder.

Another example of an augmented ECG signal appears in U.S. Pat. No. 3,923,041 issued Dec. 2, 1975 for Cardiac Signal Augmentation Apparatus by Stasz et al. This patent also recognizes the desirability of providing a uniform pacer signal in response to the detection of an original pacer pulse, which uniform pacer signal is then summed with the ECG signal from which the original pacer has been removed for subsequent use, as in telephone transmission.

Further examples of circuitry for suppressing the pacer pulse (including tail) from the ECG signal and providing a uniform artificial pacer signal or tag for recombination therewith are contained in U.S. patent applications Ser. Nos. 781,816 for Pacer Tail Suppressor filed Mar. 28, 1977 by Naylor et al and Ser. No. 760,487 for Artifact Suppression In Coronary Monitoring filed Jan. 19, 1977 by Marchese et al.

However, in all of the aforementioned patents, as well as all of the other prior art of which the applicant and his attorney are aware, the time-widened artificial pacer pulse is of constant polarity, regardless of the polarity of the pacer pulse which appeared in the originally detected ECG signal. In possibly the most common instance, that illustrated in the aforementioned Stasz et al patent and the Naylor et al application, an absolute value amplifier responds in the same manner to pacer pulses of either polarity to provide an artificial pacer pulse of constant polarity.

While the aforedescribed systems may be satisfactory in most instances for indicating the occurrence of pacer pulses, there are one or more situations in which it has been found desirable to also know the polarity of the sensed or detected pacer pulse. For example, some physicians while positioning the bipolar catheter tip of a pacemaker within the heart, rely upon a charge (+ to − or − to +) in the polarity of the sensed pacer pulse to provide an indication of the stability of the positioning of the catheter tip. Because of the difficulty in repeatedly and accurately perceiving the 1–2 millisecond pacer pulses appearing in the originally sensed ECG signal, it is desirable to provide artificial or standardized pacer pulses for addition to the ECG signal as previously discussed. However, there remains the problem that such standardized pacer signals will be of constant polarity regardless of the polarity of the detected pacer pulse.

Accordingly, it is a principal object of the present invention to provide improved cardiac instrumentation apparatus capable of generating standardized pacer pulse signals in response to the detection of pacer pulses and having, or at least being representative of, the polarity of the detected pacer pulses. It is a further object that such standardized pacer pulses of correct polarity be recombined with the ECG signal in appropriate time relationship such that they may be displayed and/or recorded as a single waveform.

These and other objects will be in part obvious and in part pointed out in greater detail hereinafter.

SUMMARY OF THE INVENTION

In accordance with the principles of the present invention, cardiac instrumentation apparatus adapted to receive at an input thereof an ECG signal containing pacer pulses and having means for processing at least either the ECG signal or the pacer pulses and further having output means for the processed signal includes the improvement wherein the processing means comprises means for detecting pacer pulses in the ECG signal and for determining the polarity of the respective detected pacer pulses; means responsive to the pacer pulse detecting and polarity determining means for generating standardized pacer pulse signals having, or representating, the polarity of the respective detected pacer pulses; and means for extending the standardized pacer pulse signals to the output means. In other words, the improved cardiac instrumentation apparatus is provided with means for determining the polarity of a pacer pulse detected in an ECG signal and for then generating a standardized pacer pulse signal of the polarity detected, or at least representative of the polarity detected. The standardized pacer pulse signal is additionally of substantially greater duration than that of the pacer pulse detected in an input ECG signal.

More specifically, pacer pulse detecting and polarity determining means include a pair of semiconductors of opposite-conductivity types connected to receive the pacer pulses and being normally biased to respective first conduction states, one semiconductor of the pair changing to a second conduction state in response to a pacer pulse of one polarity exceeding a preselected threshold and the other semiconductor changing to a respective second conduction state in response to a pacer pulse of the opposite polairty exceeding a respective threshold, the change from the first to the second conduction states being indicative of the occurrence of a pacer pulse and the relative conduction states of the pair of semiconductors following the change being indicative of pacer pulse polarity. Further circuitry insures that the pacer pulses (and not the normal ECG signal) are detected by the circuitry above.

Further, means for generating the standardized pacer pulse may comprise first and second means, such as D-type flip-flops, for generating respective first and second preliminary standardized pacer pulse signals of the same polarity (here positive), the first and second D-type flip-flops being respectively responsive to detected pacer pulses of respectively opposite polarity (here + and − respectively) for respectively generating the first or the second preliminary standardized pulses, adder means having an output and an inverting input and a noninverting input thereto, and means for operatively connecting the output of the first D-type flip-flop to the noninverting input and the output of the second D-type flip-flop to the inverting input of the adder means whereby the polarity of the standardized pacer pulse signal at the output of the adder means corresponds with that of the detected pacer pulse.

The apparatus further includes summing means for connecting an ECG channel thereof and the standardized pacer pulse signal generating means thereof to the apparatus output for summing the ECG signal with the standardized pacer pulse signal prior to output.

BRIEF DESCRIPTION OF THE DRAWINGS

FIGS. 3A and 3B respectively illustrate the input ECG signal containing pacer pulses of positive and negative polarities and an output ECG signal in which the input pacer pulses are replaced with standardized pacer marks having the same polarity as the respective input pacer pulses; and FIG. 4, including FIGS. 4A – 4J, is a waveform ladder diagram showing the time, and in some instances amplitude, relationships of various waveforms throughout the apparatus of FIGS. 1 and 2 during the time-expanded segment 4A of FIG. 3A.

DESCRIPTION OF THE PREFERRED EMBODIMENTS

Figure 1:
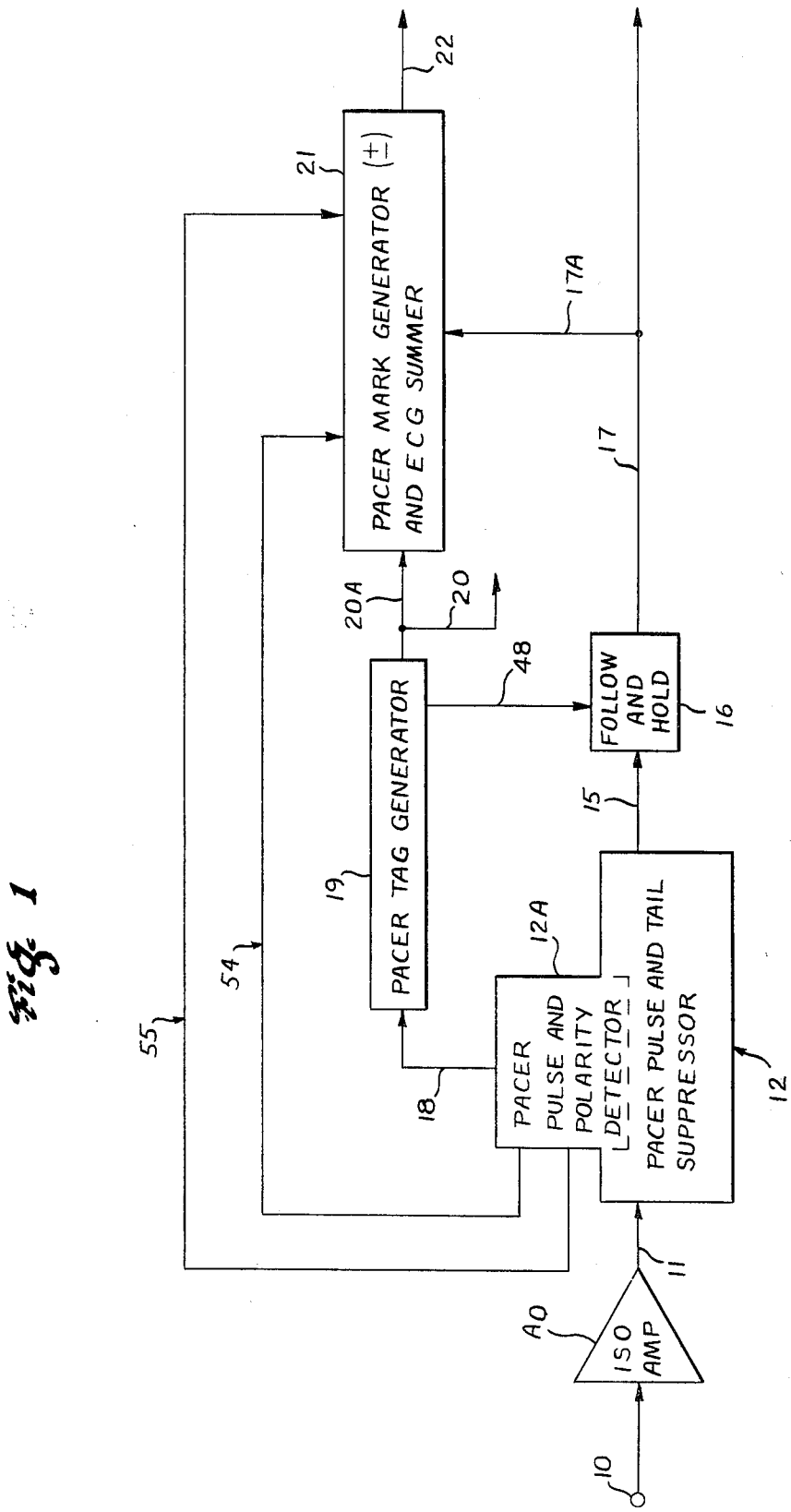
FIG. 1 is a diagrammatic representation of the cardiac instrumentation apparatus of the invention including means for generating standardized pacer signals or marks having, or representative of, the polarity of the respective pacer pulses appearing in the input ECG signal.

Referring to FIG. 1, there is illustrated an input 10 which is adapted to be connected to means such as electrodes which are in turn adapted to be connected to or placed in receiving position relative to a body for the purpose of receiving ECG signals which may include pacemaker pulses PP, as illustrated in FIG. 3A. Input 10 is connected to the input of an isolated DC amplifier $A_o$ which in turn provides electrical isolation between the patient and the circuitry beyond the output of the isolation amplifier. The output of amplifier $A_o$ is connected, as represented by line 11, to the input of pacer pulse and tail suppressor circuitry 12. Circuitry 12 is intended to remove or otherwise suppress the appearance of a pacer pulse, comprising a discharge portion (DP) and a tail or recharge waveform (RW), from the ECG signal. Suppressor circuitry 12 is preferably of the type described and illustrated in the aforementioned Naylor et al patent application, to which reference may be made for additional detail and which is incorporated herein by reference. Suppressor 12 operates to substantially remove the pacer pulse (including DP and RW), and to provide the resulting signal on output line 15 as an input to follow and hold 16. Follow and hold 16 operates to further suppress any remaining pacer "stump" and the output therefrom appearing on line 17 comprises an ECG signal with all pacer pulses suppressed.

The pacer pulse suppressor circuitry 12 includes circuitry for detecting the occurrence and polarity of a pacer pulse in the incoming ECG signal, which circuitry is designated 12A in FIG. 1. The detection of a pacer pulse serves, via line 18, to stimulate the generation of a so called pacer "tag" by pacer tag generator 19. The pacer tag signal is represented by line 20 from tag generator 19 and comprises a constant-polarity signal having a predetermined, standardized duration, "$n$", for instance 13 milliseconds. Such a pacer tag signal has heretofore been available for summation with a corresponding ECG signal for more clearly indicating the timing and existence of a corresponding pacer pulse. In the presently illustrated embodiment, the pacer tag appearing on line 20 is available for summation with an ECG signal where knowledge of pacer pulse polarity is not important; however, in accordance with the invention it is additionally available via lead 20A as an input to the pacer mark generator and ECG summer 21.

The circuitry of suppressor 12A which provides for pacer pulse detection and the pacer tag generator circuitry 19 are, in the main, identical with similar circuitry disclosed in the aforementioned Naylor et al patent application. However, the pacer mark generator 21 provides for the generation of standardized pacer signals which represent, or whose polarity corresponds with, the polarity of the respective input pacer pulses detected. Such "correct-polarity" standardized pacer pulses are, for the purposes of this description, referred to as pacer marks. Pacer marks of correct polarity might appear along on output 22 from generator 21. However in the preferred embodiment, the ECG signal 17 with pacer pulses suppressed is summed in generator 21 with the pacer mark such that the output 22 comprises an ECG signal having the respective pacer pulses now clearly marked thereon in the correct polarity in which they appear at the input 10. Such output 22 may then be used for pacer catheter positioning analysis and the like where observation of pacer pulse polarity is important. The ECG signal 17 with pacer pulses suppressed may of course be utilized for other functions, such as an input to a heart rate meter.

Figure 2:
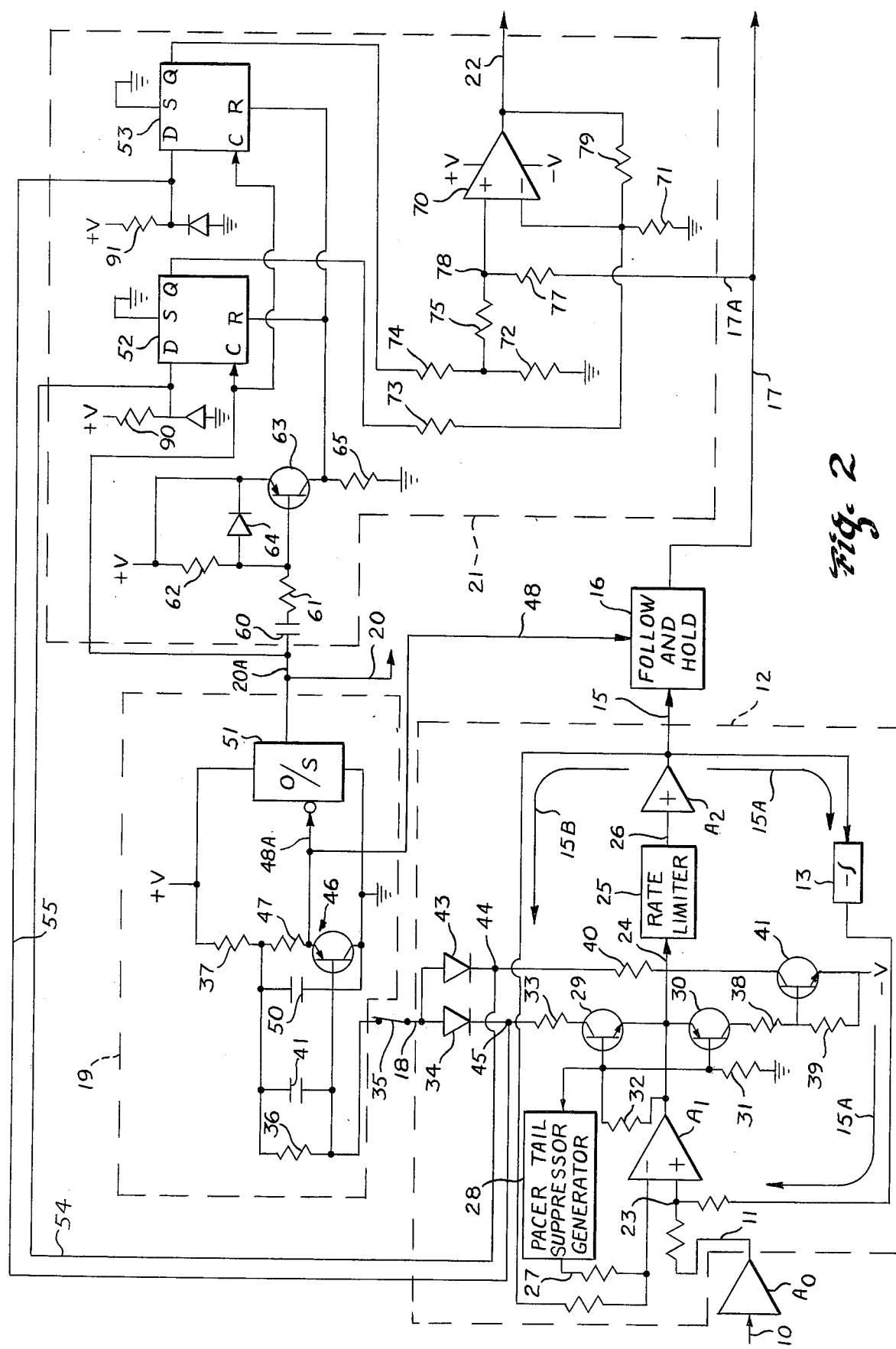
FIG. 2 is a schematic diagram of the cardiac instrumentation apparatus of the invention illustrating the improved pacer mark generating circuitry in detail.

For a better understanding of the circuitry of FIG. 1 reference is made to FIG. 2 wherein the pacer pulse and tail suppressor 12 is seen to include an operational amplifier A1 having inverting and noninverting inputs. The amplified input signal on line 11 is extended through a summing junction 23 to the noninverting input of amplifier A1. The output of amplifier A1, as presented by line 24, comprises the input to a rate limiter 25 in turn having its output 26 extended to the noninverting input of an operational amplifier A2. The output 15 from amplifier A2 comprises an input to follow and hold 16. However, the output of amplifier A2 is also utilized as, represented by arrows 15A, to provide negative feedback to the noninverting input of amplifier A1 via summing junction 23. Feedback loop 15A includes integrator 13 generally comprised of an inverting amplifier with high frequency rejection for the purpose of inverting the output of amplifier A2 for active negative feedback and emphasizing the low frequency aspects thereof. The output 27 of a pacer tail suppressor generator 28 comprises one input to the inverting input of amplifier A1 and is normally a substantially constant nominal value, except during rate limiting. The input to amplifier A1 from pacer tail suppressor generator 28 is summed with a supplemental feedback signal from the output of amplifier A2 via a passive feedback path 15B.

The rate limiter 25 is similar to that described in the aforementioned Naylor et al patent application and serves to pass the normally slowly varying ECG output of amplifier A1 to and through amplifier A2 such that the negative feedback 15A maintains a stable, small signal condition at the output of amplifier A1. However, upon the ocurrence of a pacer pulse at the input, the rate limiter is limited in its response rate and accordingly, the negative feedback via paths 15A and 15B is ineffective to balance the rapidly changing, large amplitude pacer pulse signal appearing in line 11. Accordingly, the output of amplifier A1 appearing on line 24 is no longer of small amplitude but is substantially amplified. During this period of rate limiting the output of amplifier A2 appearing on line 15 will first attempt to follow the pacer pulse, but at a greatly limited rate. Then, as the discharge portion (DW) of the pacer pulse is completed and the pulse moves to the opposite polarity at the initiation of the recharge waveform or tail (RW), a capacitor (not shown) in the rate limiter which charged during discharge portion DW empties at the rate-limited rate until rate-limiting terminates upon completion of emptying. Referring to FIG. 4, if the discharge pulse DP of the pacer pulse exists from $T_o$ to $T_2$ (i.e. 2 milliseconds) the rate limiting in one direction will occur for that same interval and will occur in the opposite direction for a similar additional interval, or from $T_2$ to $T_4$ (i.e. about an additional 2 milliseconds beyond $T_2$). This will result in a small pyramidal "stump" appearing in the output 15.

The emitters of a pair of complementary transistors 29 and 30 of opposite conductivity types (NPN and PNP respectively) are also connected to the output 24 of amplifier A1 to control the pacer tail suppression generator 28. In accordance with the invention, the complementary transistors 29 and 30 additionally assist in the detection of a pacer pulse and more specifically, in the determination of the polarity of each respective pacer pulse detected. A biasing resistor 31 is connected between ground and the base of both transistors 29 and 30 for biasing those transistors into non-conduction when the signal at the output of amplifier A1 is the normally small amplitude ECG signal which neither positively nor negatively exceeds the positive and negative threshold limits $+TH$ and $-TH$ indicated in FIG. 4B. The threshold limits comprise the $V_{be}$ drops of the respective transistors 29, 30. However, the biasing of transistors 29 and 30 is such that when rate limiting occurs and the negative feedback loops 15A and 15B are essentially opened, the greatly amplified discharge portion DP of a pacer pulse is operative to drive one or the other of the transistors 29, 30 into conduction for the interval $T_o - T_2$, depending upon its polarity. At the completion of the discharge pulse portion of the pacer signal, the feedback loops 15A and 15B continue to be open for a brief period of time (i.e. $T_2 - T_4$) and the voltage at the output of amplifier of A1 is, accordingly, of relatively large magnitude, but now of the opposite polarity represented by the recharge waveform RW. At this time (i.e. $T_2$), that one of the transistors 29, 30 which had been conducting is turned off and the other transistor is turned on to continue the input to rate limiter 25.

As described in the aforementioned Naylor et al. patent application, the output of amplifier of A1 is normally fed back to an input, in this case the inverting point, via a very large resistor 32, with relatively little control effect. However, during the discharge pulse DP portion ($T_o - T_2$) of a pacer pulse when one or the other of transistor 29, 30 is first conducting, there will be provided a low impedance path from the output of amplifier A1 through the emitter-base circuit of the conducting transistor to the input of the tail suppressor generator 28. During this interval a capacitor (not shown) in the tail suppressor generator 28 is rapidly charged to a level representative of the energy contained in the discharge pulse portion DP of the pacer pulse. Subsequently, following determination of rate limiting at $T_4$, the transistors 29, 30 again return to non-conduction and the charged capacitor in tail suppressor generator 28 begins to discharge with a relatively long time constant via line 27 into the inverting input of amplifier A1. The circuit constant of tail suppressor generator 28 are selected such that the time constant corresponds substantially with that of the tail or recharge waveform RW of the pacer pulse. Because this decaying signal is applied to the inverting input of amplifier A1, it acts to cancel or, in effect, suppress the tail or recharge waveform RW otherwise appearing in the ECG signal.

The transistors 29, 30 are also used as the origin for a control signal for generating a standardized pacer pulse and additionally a pair of control signals for indicating respectively positive or negative polarity of the pacer pulse detected. A relatively positive quiescent voltage appears on the collector of transistor 29 when it is not conducting. This voltage results from the connection of resistor 33 from the collector of transistor 29 to the cathode of diode 34, in turn having its anode connected via line 18 through normally closed switch 35 and series resistors 36 and 37 to a source of positive voltage $+V$ (i.e. $+15$ volts). Switch 35 permits selective disconnection of the pacer tag and mark generating circuitry which follows. Similarly, when transistor 30 is non-conducting, as is usually the case, it has a normally negative voltage applied to its collector via series resistors 38 and 40 connected to a source of negative voltage $-V$ (typically $-15$ volts). Further, an inverting transistor 41 has its emitter connected to $-V$ and its base connected to the junction of resistors 38 and 40 and its collector connected to one end of resistor 42, the other end of which is connected to the cathode of diode 43 having its anode connected to the anode of diode 34 and thus, through switch 35 and resistors 36, 37 to $+V$. Diodes 34 and 43 serve to mutually isolate the collector circuits of transistors 29 and 30 from one another. Inverter 41 enables the signal resulting from the conduction of transistor 30 and appearing at junction 44 of the cathode of diode 43 to be of comparable polarity and voltage to the signal resulting at junction 45 at the cathode of diode 34 when transistor 29 conducts.

Junctions 44 and 45 are both normally at positive potentials of about $+V$ and each moves relatively more negative, to ground potential or slightly below, when its respective transistor 30 or 29 conducts. A pair of pull-up resistors 90 and 91 (shown at D inputs to D-flops 52,53) connected to junctions 44 and 45 respectively maintain the collector of non-conducting one of transistors 29, 30 near +V. Because transistors 29 and 30 conduct in alternation with one another from intervals $T_o$ to $T_2$ and $T_2$ to $T_4$, the relatively lower potentials appearing at junctions 44 and 45 are similarly in alternation with one another. Assuming a positive pacer pulse as illustrated in FIG. 4A, the transistor 30 will first be biased into conduction at time $T_o$, thereby lowering the voltage at junction 44 as illustrated in FIG. 4D. Subsequently, at time $T_2$, the transistor 30 will be turned of and the negative-polarity recharge waveform RW will briefly turn on transistor 29 for the interval $T_2 - T_4$ during which the potential at junction 45 is relatively lowered, as illustrated in FIG. 4C.

A control signal indicative of both the occurrence of a pacer pulse and of the length of an interval comparable to about twice the $T_o - T_2$ interval of the discharge pulse portion thereof (i.e. $T_o - T_4$) is obtained from the voltage appearing at the anodes of diodes 34, 43. This potential is applied to the base of a transistorized emitter follower 46 having its collector connected to ground and its emitter connected through series resistors 47 and 37 to +V. The potential appearing at the base of emitter follower 46, and accordingly at the emitter output thereof, is normally high and goes to a relatively lower voltage for the interval $T_o - T_4$.

The relatively negative step on the emitter of transistor 46 at $T_o$ is capacitively coupled (capacitor not shown) via line 48 to the control electrode of a gate within follow and hold 16 for preventing passage of the remaining "stump" in the ECG signal on lead 15 from appearing in the ECG signal appearing at the output of the follow and hold on lead 17. Capacitors 49 and 50 connected in the base-emitter and collector-emitter circuits respectively of emitter follower 46 serve to insure that the emitter follower does not briefly return to non-conduction in the brief interval between turn off of one of transistors 29, 30 and the turn on of the other and maintain the FET gate (not shown) in follow and hold 16 non-conducting for an interval somewhat longer that $T_o - T_4$.

The waveform of the potential appearing at the emitter of emitter follower 46 is illustrated in FIG. 4E and serves also, via lead 48A to trigger the one-shot 51 of pacer tag generator 19. The one-shot 51 is of the type which responds only to a negative-going step for generating a positive output pulse of preselected duration. Accordingly, when the potential on the emitter of the emitter follower 46 makes a relatively negative step at $T_o$ with the initiation of conduction in one of the transistors 29, 30 (30 in the illustrated example), the one-shot 51 will respond by generating a so-called pacer tag signal of preselected duration and appearing on output lead 20 therefrom. The signal appearing on output lead 20 from one-shot 51 is normally a logic "0" and moves to a logic "1" to produce the pacer tag, as illustrated in FIG. 4F. The duration of the pacer tag will be substantially longer than that of the 2 milliseconds duration of the discharge pulse portion of the pacer pulse and is here designated by $T_n$. Typically the pacer tag will exist for an interval of about 13 milliseconds. Such pacer tags of predetermined duration and singular polarity have been known, as mentioned earlier. It should be noted that the "predetermined duration" of a pacer tag may be a function of the pacer pulse duration rather than a fixed value, such as discussed in the aforementioned Day patent.

However, in accordance with the invention, the output of one-shot 51 is extended via lead 20A to the respective clock inputs C of a pair of D-type flip flops (D-flop) 52 and 53. The Q output of a D-flop is determined by the D input that appeared one clock pulse earlier; for example, if a logic "1" appeared at the gate input D, the output at Q after the next clock pulse would be a logic "1". Accordingly, if a logic "0" appeared at the D input to a D-flop, the next following clock pulse will result in a logic "0" appearing at the Q output. The D inputs to D-flops 52 and 53 are applied via leads 54 and 55 from junctions 44 and 45 respectively. The potential at junctions 44 and 45 are normally high (logic "1") prior to the occurrence of any particular pacer pulse. The Q output of the respective D-flops 52 and 53 will however normally be logic "0" as a result of having been rest to that condition, as will be hereinafter explained. Thus, when one-shot 51 generates a positive pacer tag pulse, the positive going transition of that pulse appearing on lead 20A will be operative to generate a logic "1" at the Q output of either D-flop 52, 53 having a logic "1" applied to its input immediately prior thereto. However, only one of the two D-flops will at that time generate a logic "1" at its Q output inasmuch as the D input to the other D-flop will have gone to logic "0" immediately prior to being clocked. This situation arises from the fact that one or the other of the junctions 44, 45 had to move negatively (i.e. to logic "0") in order to provide the negative trigger to the input of one-shot 51 which results in the generation of the clock.

It should be noted that a positive pacer pulse, as illustrated in FIG. 4A results in the conduction of transistor 30 and accordingly, the decrease in voltage at junction 44, which in turn means that the D input of D-flop 52 will be at logic "0" and the D input of D-flop 53 will be at logic "1" at the moment their clock inputs receive a positive-going clock from the output of one-shot 51. Accordingly, only the Q output of D-flop 53 will go from a logic "0" to a logic "1" state at time $T_o$, the Q output of D-flop 52 remaining at the logic "0" level to which it had been reset. There is no other positive-going output from one-shot 51 until the next pacer pulse is recognized. Therefore, even though transistor 29 conducts between $T_2 - T_4$ and transistor 30 is non-conducting during that interval, there will be no change in the outputs of D-flops 52, 53 inasmuch as no clock pulse occurs.

Thus, for a positive pacer pulse as illustrated in FIG. 4A the output of D-flop 53 is a logic "1" as illustrated in FIG. 4H and the output of D-flop 52 is a logic "0" as illustrated in FIG. 4I. It will be appreciated that this relationship would have been reversed if the discharge pulse portion DP of the pacer pulse had been in a negative direction rather than positive. The logic "1" output from one of the D-flops 52, 53 immediately following the detection of a pacer pulse comprises a pacer mark which may be utilized in a variety of ways and has some standardized duration which preferably, though not necessarly, corresponds with that of the pacer tag from one-shot 51. In the illustrated embodiment the pacer mark appearing at the output of either D-flop 52 or 53 has substantially the same duration as the pacer tag as a result of the timing of the reset pulse, illustrated in FIG. 4G, which resets D-flops 52, 53.

The reset pulse is obtained by extending the pacer tag signal via lead 20A through a differentiator and an inverter to the respective reset inputs R of D-flops 52, 53. The differentiator is comprised of a capacitor 60, a base current limiting resistor 61, and a resistor 62 connected to +V. The differentiated leading and trailing edges of the pacer tag signal comprise respectively positive and negative pulses applied to the base of transistor inverter 63 at the junction of resistors 61, 62. A clamping diode 64 has its anode connected to the base of transistor 63 and its cathode connected to the emitter and +V for preventing damage to transistor 63 as a result of excessive positive voltage. A pull down resistor 65 extends between the collector of transistor 63 and ground. Transistor 63 is normally biased out of conduction, such that its collector output is substantially at ground, and is turned on to provide a relatively more positive output only in response to a negative input pulse resulting from the differentiation of the trailing or final edge of a respective pacer tag signal. This positive pulse at the output of inverter 63 is of relatively short duration and is operative to reset the Q outputs of both D-flops 52, 53 to the logic "0" level to await detection of the next pacer pulse.

In the broadest scope of the invention, the outputs of the respective D-flops 52, 53 are indicative or representative of both the occurrence of a pacer pulse and additionally the polarity of the pacer pulse detected. This is true even though the outputs of D-flops 52, 53 may only vary between a logic "0" and a logic "1". As previously discussed, only the output of D-flops 53 goes to a logic "1" if the detected pacer pulse is of positive polarity and conversely, only the output of D-flop 52 goes to logic "1" if the detected pacer pulse is of negative polarity. Therefore the outputs of D-flops 52, 53 may be used as respective inputs to various types of equipment capable of indicating or generating a positive pacer mark if D-flop 53 provides a logic "1" output and a negative pacer mark if D-flop 52 provides a logic "1" output. However in the illustrated embodiment the function of generating a pacer mark of the correct polarity is provided within the described apparatus in the form of an adder.

The adder comprises an operational amplifier 70 having inverting and noninverting inputs to which the Q outputs of D-flops 52 and 53 respectively are connected through summing resistors. Amplifier 70 is connected to sources of positive and negative voltage relative to ground, i.e. for instance +V and −V. The Q output of D-flop 52 is extended via summing resistor 73 (270 k ohms) to the inverting input of amplifier 70. The Q output of D-flop 53 extends to the noninverting input of amplifier 70 through summing resistor 74 (about 390 k ohms) in series with summing resistor 75 (10 k ohms). Attenuating resistor 72 (about 22 k ohms) extends from the junction of resistor 74, 75 to ground. Feedback resistors 79 and 71 (about 4 k ohms and 15 k ohms respectively) are operatively connected between the output 22 and the inverting input of amplifier 70 and ground for determining the gain of the adder.

When a pacer pulse is detected, the output of one of D-flops 52, 53 provides a substantially grounded or "0" input at one input to the adder and the output of the other D-flop provides a positive or logic "1" input at the other adder input. If D-flop 53 provided the logic "1" input, then the output 22 from amplifier 70, and thus the adder, will reflect a positive pacer mark. If, on the other hand, D-flop 52 provides a logic "1" input and is applied to the inverting input of the adder the output 22 will be a negative pacer mark. Thus, the pacer mark appearing at output 22 will be of the polarity of the pacer pulse detected.

While the adder might simply provide a pacer mark of correct polarity on output 22 for whatever subsequent use, the illustrated embodiment prefers combining the pacer mark with the "clean" ECG signal appearing on line 17 so that the combined signal may be provided as an output from the present apparatus. Accordingly, the ECG signal on line 17 (with pacer pulse and tail suppressed) is extended via lead 17A through summing resistor 77 (10 k ohms) to the summing junction 78 at the noninverting input to amplifier 70. The output 22 from the adder then comprises the ECG signal received at input 10, but with the original pacer pulses replaced by standardized pacer pulses of the same polarity as the original pulse, as illustrated in FIG. 3B.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. In cardiac instrumentation apparatus adapted to receive at an input thereof an ECG signal containing pacer pulses, means for processing at least either said ECG signal or said pacer pulses, and output means for the processed signal, the improvement wherein said processing means comprises:
   means for detecting pacer impulses in said ECG signal and for determining the polarity of the respective said detected pacer pulses;
   means responsive to said pacer pulse detecting and polarity determining means for generating respective standardized pacer pulse signals representative of the polarity of the respective said detected pacer pulses; and
   means for extending said standardized pacer pulse signals to said output means.

2. The cardiac instrumentation apparatus of claim 1 wherein said pacer pulse detecting and polarity determining means comprises a pair of opposite-conductivity type semiconductors, both semiconductors of said pair being operatively connected to receive said pacer pulse and being normally biased to respective first conduction states, one semiconductor of said pair changing to a second conduction state in response to the occurrence of a pacer pulse of one polarity exceeding a threshold and the other semiconductor of said pair changing to a respective second conduction state in response to the occurrence of a pacer pulse of the opposite polarity exceeding a respective threshold, a said change from said first to said second conduction state being indicative of the occurrence of a pacer pulse and the relative conduction states of said pair of semiconductors following said conduction-change being indicative of pacer pulse polarity.

3. The cardiac instrumentation apparatus of claim 1 wherein said standardized pacer pulse generating means comprises first and second means for generating respective first and second standardized pacer pulse signals of the same polarity at respective outputs thereof, said first and second means being respectively responsive to detected pacer pulses of respectively opposite polarity for respectively generating said first or said second standardized pacer pulses, a said standardized pacer pulse signal appearing at the output of said first means being representtive of a pacer pulse of one polarity and a said standardized pacer pulse signal appearing at the output of said second means being representative of a pacer pulse having a polarity opposite that represented by said first means.

4. The cardiac instrumentation apparatus of claim 3 wherein said first and second standardized pacer pulse signals respectively comprise first and second preliminary standardized pacer pulse signals and further including adder means having an output and an inverting input and a noninverting input thereto, means for operatively connecting the output of said first means to one said input of said adder means and means for operatively connecting the output of said second means to the other said input of said adder means whereby the polarity of said standardized pacer pulse signal at the output of said adder means corresponds with that of said detected pacer pulse.

5. The cardiac instrumentation apparatus of claim 4 including ECG channel means operatively connected to said apparatus input, and summing means connecting said ECG channel means and the output of said first means to said one said input of said adder means for summing said first preliminary standardized pacer pulse signal with the ECG signal and applying said summed signal as the input to said one said input of said adder means.

6. The cardiac instrumentation apparatus of claim 5 wherein said first and second preliminary standardized pacer pulse signals are of positive polarity, said first means is responsive to detected pacer pulses only of positive polarity, and said one of said input of said adder means to which said summing means is connected is noninverting.

7. The cardiac instrumentation apparatus of claim 1 wherein said standardized pacer pulse signal is of substantially greater duration than said respective pacer pulses detected.

8. The cardiac instrumentation apparatus of claim 1 including ECG channel means operatively connected to said apparatus input, summing means connecting said ECG channel means and said standardized pacer pulse signal generating means to said apparatus output for summing the ECG signal with said standardized pacer pulse signal prior to output.

* * * * *

UNITED STATES PATENT AND TRADEMARK OFFICE
CERTIFICATE OF CORRECTION

PATENT NO. : 4,117,848
DATED : October 3, 1978
INVENTOR(S) : Thomas Kipling Naylor It is certified that error appears in the above–identified patent and that said Letters Patent are hereby corrected as shown below:

In column 1, line 52, after "pacer", insert --pulse--;

In column 4, line 44, delete "along" and insert --alone--.

Signed and Sealed this

Twentieth Day of February 1979

[SEAL]

Attest:

RUTH C. MASON
Attesting Officer

DONALD W. BANNER
Commissioner of Patents and Trademarks